United States Patent
Hassantabar et al.

(10) Patent No.: US 12,383,206 B2
(45) Date of Patent: *Aug. 12, 2025

(54) SYSTEM AND METHOD FOR TESTING FOR SARS-COV-2/COVID-19 BASED ON WEARABLE MEDICAL SENSORS AND NEURAL NETWORKS

(71) Applicant: The Trustees of Princeton University, Princeton, NJ (US)

(72) Inventors: Shayan Hassantabar, Ewing, NJ (US); Niraj K. Jha, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 378 days.

This patent is subject to a terminal disclaimer.

(21) Appl. No.: 17/923,958

(22) PCT Filed: Apr. 20, 2021

(86) PCT No.: PCT/US2021/028088
§ 371 (c)(1),
(2) Date: Nov. 8, 2022

(87) PCT Pub. No.: WO2021/231044
PCT Pub. Date: Nov. 18, 2021

(65) Prior Publication Data
US 2023/0181120 A1    Jun. 15, 2023

Related U.S. Application Data

(60) Provisional application No. 63/022,997, filed on May 11, 2020, provisional application No. 63/053,912, filed on Jul. 20, 2020.

(51) Int. Cl.
*A61B 5/00* (2006.01)
*A61B 5/0205* (2006.01)
(Continued)

(52) U.S. Cl.
CPC .......... *A61B 5/7267* (2013.01); *A61B 5/0205* (2013.01); *A61B 5/0533* (2013.01); *G16H 10/20* (2018.01); *G16H 50/80* (2018.01)

(58) Field of Classification Search
CPC ... A61B 5/7267; A61B 5/0205; A61B 5/0533; G16H 50/80; G16H 10/20
See application file for complete search history.

(56) References Cited

U.S. PATENT DOCUMENTS

| | | |
|---|---|---|
| 2014/0247151 A1 | 9/2014 | Proud et al. |
| 2018/0353085 A1 | 12/2018 | Olivero |

OTHER PUBLICATIONS

Thomas, Journal of Biomedical Informatics, Apr. 2021, pp. 1-22.*

(Continued)

*Primary Examiner* — Michael I Ezewoko
(74) *Attorney, Agent, or Firm* — MEAGHER EMANUEL LAKS GOLDBERG & LIAO, LLO

(57) ABSTRACT

According to various embodiments, a machine-learning based system for coronavirus detection is disclosed. The system includes one or more processors configured to interact with a plurality of wearable medical sensors (WMSs). The processors are configured to receive physiological data from the WMSs and questionnaire data from a user interface. The processors are further configured to train at least one neural network based on raw physiological data and questionnaire data augmented with synthetic data and subjected to a grow-and-prune paradigm to generate at least one coronavirus inference model. The processors are also configured to output a coronavirus-based decision by inputting the received physiological data and questionnaire data into the generated coronavirus inference model.

38 Claims, 12 Drawing Sheets

(51) Int. Cl.
  *A61B 5/0533* (2021.01)
  *G16H 10/20* (2018.01)
  *G16H 50/80* (2018.01)

(56) References Cited

OTHER PUBLICATIONS

Pratama, Neurocomputing, 2017, pp. 4-27.*
Dail, ArXiv, 2018, pp. 1-13.*
International Search Report and Written Opinion for corresponding PCT Application No. PCT/US2021/028088, dated Jul. 16, 2021.
Landi, "Boston startup using AI, remote monitoring to fight coronavirus", fiercehealthcare.com, [online] [retrieved on Jun. 16, 2021 (Jun. 16, 2021)) Retrieved from the Internet < URL: https://www.fiercehealthcare.com/techlboston-startup-using-ai-remote-monitoring-to-fightcoronavirus, Mar. 6, 2020.
Yin et al., "DiabDeep: Pervasive Diabetes Diagnosis based on Wearable Medical Sensors and Efficient NeuralNetworks", Cornell University Library/Computer Science/Computer Vision and Pattern Recognition, (online) (retrieved on Jun. 16, 2021 (Jun. 16, 2021)] Retrieved from the Internet< URL: https:/farxiv.org/abs/1910.04925, Oct. 11, 2019.
Hassantabar et al., "SCANN: Synthesis of compact and accurate neural networks", arXiv preprint arXiv.1904.09090, 2019.
Dai et al., "NeST: A neural network synthesis tool based on a grow-and-prune paradigm", IEEE Trans. Computers, vol. 68, No. 10, pp. 1487-1497, Oct. 2019.
Hassantabar, Shayan et al., "TUTOR: Training Neural Networks Using Decision Rules as Model Priors," arXiv:2010.05429, Oct. 2020.
Hassantabar, Shayan et al., "SCANN: Synthesis of compact and accurate neural networks," arXiv: 1904.09090, Apr. 2019.
Dai, Xiaoliang et al., "NeST: A neural network synthesis tool based on a grow-and-prune paradigm", IEEE Trans. Computers, vol. 68, No. 10, pp. 1487-1497, Oct. 2019.
Dheda, Keertan et al., "Diagnosis of COVID-19: Considerations, Controversies and Challenges in South Africa," Wits Journal of Clinical Medicine, vol. 2, No. SI, pp. 3-10, 2020.
Bullock, Joseph et al., "Mapping the landscape of artificial intelligence applications against COVID-19," Journal of Artificial Intelligence Research, vol. 69, pp. 807-845, Nov. 2020.
Farooq, Muhammad and Hafeez, Abdul, "COVID-ResNet: A Deep Learning Framework for Screening of COVID19 from Radiographs," arXiv:2003.14395, 2020.
Wang, Linda et al., "COVID-Net: A tailored deep convolutional neural network design for detection of COVID-19 cases from chest radiography images," Scientific Reports, vol. 10, No. 19549, 2020.
Giovagnoni, A. and Agostini, A., "Diagnosi radiologica e prevenzione della diffusione di COVID-19 nei dipartmenti di radiologia," SIRM, 2020, online: https://www.sirm.org/wp-content/uploads/2020/03/SIRM-Covid-19.pdf.
Zhang, Jianpeng et al., "COVID-19 Screening on Chest X-ray Images Using Deep Learning based Anomaly Detection," arXiv:2003.12338v1, Mar. 27, 2020.
Narin, Ali et al., "Automatic detection of coronavirus disease (COVID-19) using X-ray images and deep convolutional neural networks," Pattern Analysis and Applications, vol. 24, pp. 1207-1220, May 9, 2021.
Abbas, Asmaa et al., "Classification of COVID-19 in chest X-ray images using DeTraC deep convolutional neural network," Applied Intelligence, vol. 51, pp. 854-864, Sep. 5, 2020.
Hall, Lawrence O. et al., "Finding COVID-19 from Chest X-rays using Deep Learning on a Small Dataset," arXiv:2004.02060, 2020.
Sethy, Prabira Kumar and Behera, Santi Kumari, "Detection of coronavirus disease (COVID-19) based on Deep Features," Preprints, vol. 2020030300, 2020.
Li, Lin et al., "Artificial Intelligence Distinguishes COVID-19 from Community Acquired Pneumonia on Chest CT," Radiology, p. 200905, 2020.
Gozes, Ophir et al., "Rapid AI development cycle for the coronavirus (COVID-19) pandemic: Initial results for automated detection & patient monitoring using deep learning CT image analysis," arXiv:2003.05037, 2020.
Apostolopoulos, Ioannis D. and Mpesiana, Tzani A., "COVID-19: Automatic detection from X-ray images utilizing transfer learning with convolutional neural networks," Physical and Engineering Sciences in Medicine, vol. 43, pp. 635-640, Apr. 3, 2020.
Wang, Shuo et al., "A fully automatic deep learning system for COVID-19 diagnostic and prognostic analysis," European Respiratory Journal, vol. 56, No. 2000775, 2020.
Afshar, Parnian et al., "COVID-CAPS: A capsule network-based framework for identification of COVID-19 cases from X-ray images," Pattern Recognition Letters, vol. 138, pp. 638-643, Sep. 16, 2020.
Kalkreuth, Roman and Kaufmann, Paul, "COVID-19: A Survey on Public Medical Imaging Data Resources," arXiv:2004.04569v2, May 9, 2020.
Cohen, Joseph Paul et al., "COVID-19 Image Data Collection," arXiv:2003.11597v1, Mar. 25, 2020.
Lin, MD, Liaoyi et al., "CT Manifestations of Coronavirus Disease (COVID-19) Pneumonia and Influenza Virus Pneumonia: A Comparative Study," AJR, vol. 216, pp. 71-79, Jul. 9, 2020.
Imran, Ali et al., "AI4COVID-19: AI enabled preliminary diagnosis for COVID-19 from cough samples via an app," Informatics in Medicine Unlocked, vol. 20, No. 100378, Jun. 26, 2020.
Sandler, Mark et al., "MobileNetV2: Inverted Residuals and Linear Bottlenecks," arXiv:1801.04381v4, Mar. 21, 2019.
Ma, Ningning et al., "ShuffleNet V2: Practical Guidelines for Efficient CNN Architecture Design," arXiv: 1807.11164v1, Jul. 30, 2018.
Wu, Bichen et al., "Shift: A Zero FLOP, Zero Parameter Alternative to Spatial Convolutions," arXiv:1711.08141v2, Dec. 3, 2017.
Dai, Xiaoliang et al., "ChamNet: Towards Efficient Network Design through Platform-Aware Model Adaptation," arXiv: 1812.08934v1, Dec. 21, 2018.
Hassantabar, Shayan et al., "Steerage: Synthesis of Neural Networks Using Architecture Search and Grown-and-Prune Methods," arXiv: 1912.05831v1, Dec. 12, 2019.
Han, Song et al., "Deep Compression: Compressing Deep Neural Networks with Pruning, Trained Quantization and Huffman Coding," arXiv: 1510.00149v5, Feb. 15, 2016.
Han, Song et al., "ESE: Efficient Speech Recognition Engine with Sparse LSTM on FPGA," arXiv: 1612.00694v2, Feb. 20, 2017.
Dai, Xiaoliang et al., "Grow and Prune Compact, Fast, and Accurate LSTMs," arXiv: 1805.11797v2, May 31, 2018.
Zhu, Chenzhuo et al., "Trained Ternary Quantization," arXiv: 1612.01064v3, Feb. 23, 2017.
Krizhevsky, Alex et al., "ImageNet Classification with Deep Convolutional Neural Networks," Proceedings of Advances in Neural Information Processing Systems, pp. 1097-1105, 2012.
Grossberg, Stephen, "Nonlinear Neural Networks: Principles, Mechanisms, and Architectures," Neural Networks, vol. 1, pp. 17-61, 1988.
World Health Organization and Others, "Coronavirus disease 2019 (COVID-19): Situation report—72," Apr. 1, 2020, online: https://apps.who.int/iris/bitstream/handle/10665/331685/nCoVsitrep01Apr2020-eng.pdf.
Mahase, Elisabeth, "Coronavirus: covid-19 has killed more people than SARS and MERS combined, despite lower case fatality rate," The British Medical Journal, vol. 368, Feb. 18, 2020.
Nicola, Maria et al., "The socio-economic implications of the coronavirus pandemic (COVID-19): A review," International Journal of Surgery, vol. 78, pp. 185-193, 2020.
Butt, Charmaine et al., "Deep learning system to screen coronavirus disease 2019 pneumonia," Applied Intelligence, Apr. 22, 2020.
Yin, Hongxu and Jha, Niraj K., "A Health Decision Support System for Disease Diagnosis Based on Wearable Medical Sensors and Machine Learning Ensembles," IEEE Transactions on Multi-Scale Computing Systems, vol. 3, No. 4, pp. 228-241, Oct.-Dec. 2017.
Wang, Lucy Lu et al., "CORD-19: The COVID-19 Open Research Dataset," arXiv:2004.10706v4, Jul. 10, 2020.

* cited by examiner

Algorithm 1: Connection growth algorithm

Input: $W \in R^{M \times N}$: weight matrix of dimension $M \times N$ (connecting layer with $M$ neurons to layer with $N$ neurons); $Mask \in R^{M \times N}$: weight mask of the same dimension as the weight matrix; Network $P$; $W.grad$: gradient of the weight matrix (of dimension $M \times N$); data $D$; $\alpha$: growth ratio
if full growth then
    $Mask_{[1:M, 1:N]} = 1$
else if gradient-based growth then
    Forward propagation of data $D$ through network $P$ and then back propagation
    Accumulation of $W.grad$ for one training epoch
    $t = (\alpha \times MN)^{th}$ largest element in the $|W.grad|$ matrix
    for all $w.grad_{ij}$ do
      if $|w.grad_{ij}| > t$ then
        $Mask_{ij} = 1$
      end if
    end for
else if
    $W = W \otimes Mask$
Output: Modified weight matrix $W$ and mask matrix $Mask$

*FIG. 5*

Algorithm 2: Connection pruning algorithm

Input: Weight matrix $W \in R^{M \times N}$; mask matrix $Mask$ of the same dimension as the weight matrix; $\alpha$: pruning ratio
$t = (\alpha \times MN)^{th}$ largest element in $|W|$
for all $w_{ij}$ do
   if $|w_{ij}| < t$ then
      $Mask_{ij} = 0$
   end if
end for
$W = W \otimes Mask$
Output: Modified weight matrix $W$ and mask matrix $Mask$

*FIG. 6*

Algorithm 3: Neuron growth algorithm

Input: Network $P$; weight matrix $W \in R^{M \times N}$; mask matrix *Mask* of the same dimension as the weight matrix; data $D$; candidate neuron $n_j$ to be added; array $A$ of activation values for all hidden neurons
if activation-based selection then
    Forward propagation through $P$ using data $D$
    $i = argmax$ (A)
else if random selection then
    randomly pick an active neuron $n_i$
end if
$Mask_{j\cdot} = Mask_{i\cdot}$, $Mask_{\cdot j} = Mask_{\cdot i}$
$w_{j\cdot} = w_{i\cdot} + noise$, $w_{\cdot j} = w_{\cdot i} + noise$
Output: Modified weight matrix $W$ and mask matrix *Mask*

*FIG. 7*

Data Types Collected in the CovidDeep Framework

| Data Type | Data Source |
|---|---|
| Immune-compromised | Questionnaire |
| Chronic Lung Disease | Questionnaire |
| Shortness of Breath | Questionnaire |
| Cough | Questionnaire |
| Fever | Questionnaire |
| Muscle Pain | Questionnaire |
| Chills | Questionnaire |
| Headache | Questionnaire |
| Sore Throat | Questionnaire |
| Smell/Taste Loss | Questionnaire |
| Diarrhea | Questionnaire |
| Galvanic Skin Response ($\mu S$) | Smartwatch |
| Skin Temperature (°C) | Smartwatch |
| Inter-beat Interval (ms) | Smartwatch |
| Oxygen Saturation (%) | Pulse Oximeter |
| Systolic Blood Pressure (mmHg) | Blood Pressure Monitor |
| Diastolic Blood Pressure (mmHg) | Blood Pressure Monitor |

*FIG. 8*

Confusion Matrix for the Most Accurate
Three-way Classification Model

| Label ↓ \ Prediction → | C1 | C2 | C3 | Total |
|---|---|---|---|---|
| C1 | 1066 | 9 | 0 | 1075 |
| C2 | 54 | 1152 | 0 | 1206 |
| C3 | 0 | 0 | 975 | 975 |
| Total | 1120 | 1161 | 975 | 3256 |

*FIG. 9*

Test Accuracy, FPR, FNRs, and F1 Score (All in %) for the
Three DNN Models Obtained for the Most Accurate Case

| DNN Model Trained On | Acc. | FPR | FNR(2) | FNR(3) | F1 Score |
|---|---|---|---|---|---|
| Real Training Dataset | 79.9 | 22.5 | 34.2 | 0.0 | 80.9 |
| Real+Synthetic Training Dataset | 84.8 | 14.1 | 28.4 | 0.0 | 85.5 |
| Real+Synthetic Training Dataset+Grow-Prune | 98.1 | 0.8 | 4.5 | 0.0 | 98.2 |

*FIG. 10*

Test Accuracy, FPR, FNRs, and F1 Score (All in %)
for Two DNN Models Obtained for Feature Subsets from One, Two or Three Data Categories

| Data Category | DNN Model 1 | | | | | DNN Model 2 | | | | |
|---|---|---|---|---|---|---|---|---|---|---|
| | Acc. | FPR | FNR(2) | FNR(3) | F1 Score | Acc. | FPR | FNR(2) | FNR(3) | F1 Score |
| GSR | 54.2 | 22.1 | 23.3 | 99.6 | 44.6 | 54.2 | 22.1 | 23.4 | 99.5 | 44.7 |
| Temp | 57.2 | 31.5 | 60.3 | 33.4 | 57.5 | 58.6 | 32.2 | 60.2 | 28.2 | 58.7 |
| IBI | 66.6 | 55.1 | 24.0 | 21.1 | 65.6 | 66.8 | 53.1 | 25.1 | 21.1 | 66.0 |
| Ox | 45.4 | 56.2 | 59.6 | 46.7 | 45.5 | 45.4 | 56.2 | 59.6 | 46.7 | 45.5 |
| BP | 44.3 | 96.3 | 60.3 | 5.2 | 36.4 | 44.3 | 96.3 | 60.3 | 5.2 | 36.4 |
| Q | 61.4 | 0.0 | 100.0 | 5.2 | 53.5 | 63.0 | 0.0 | 100.0 | 0.0 | 54.7 |
| GSR+Temp | 57.2 | 33.4 | 60.3 | 31.4 | 57.3 | 76.9 | 6.4 | 44.1 | 15.4 | 76.5 |
| GSR+IBI | 74.9 | 3.2 | 34.6 | 37.4 | 74.3 | 76.1 | 3.6 | 31.9 | 36.3 | 75.5 |
| GSR+Ox | 52.7 | 29.0 | 44.2 | 71.3 | 51.3 | 47.5 | 44.3 | 44.7 | 71.3 | 46.1 |
| GSR+BP | 55.2 | 70.7 | 53.8 | 5.2 | 52.7 | 64.1 | 46.4 | 51.2 | 5.2 | 63.7 |
| GSR+Q | 89.1 | 6.8 | 23.3 | 0.0 | 89.6 | 89.2 | 6.7 | 23.3 | 0.0 | 89.7 |
| Temp+IBI | 68.1 | 19.3 | 53.9 | 18.8 | 68.4 | 68.2 | 19.9 | 52.9 | 18.9 | 68.6 |
| Temp+Ox | 48.3 | 26.3 | 78.4 | 46.7 | 46.5 | 49.3 | 24.2 | 77.7 | 46.7 | 47.3 |
| Temp+BP | 50.3 | 84.5 | 54.7 | 5.2 | 45.9 | 53.7 | 74.0 | 54.7 | 5.2 | 50.9 |
| Temp+Q | 68.9 | 26.5 | 60.4 | 0.0 | 69.8 | 69.0 | 26.3 | 60.3 | 0.0 | 69.9 |
| IBI+Ox | 48.1 | 60.4 | 68.0 | 22.7 | 49.8 | 49.0 | 58.3 | 68.0 | 22.1 | 50.7 |
| IBI+BP | 47.8 | 92.8 | 54.0 | 5.2 | 44.8 | 48.5 | 89.8 | 54.9 | 5.2 | 46.3 |
| IBI+Q | 80.9 | 19.5 | 34.2 | 0.0 | 81.8 | 80.9 | 17.8 | 35.8 | 0.0 | 81.7 |
| Ox+BP | 59.6 | 56.2 | 54.8 | 5.2 | 59.1 | 66.9 | 56.2 | 35.8 | 5.2 | 66.8 |
| Ox+Q | 50.2 | 56.2 | 80.2 | 5.2 | 52.5 | 50.2 | 56.2 | 80.2 | 5.2 | 52.5 |
| BP+Q | 51.8 | 56.2 | 80.1 | 0.0 | 49.9 | 57.6 | 56.2 | 60.3 | 5.2 | 56.8 |
| GSR+Temp+IBI | 70.5 | 11.5 | 54.7 | 17.9 | 70.8 | 76.6 | 3.5 | 46.0 | 17.2 | 76.7 |
| GSR+Temp+Ox | 69.1 | 22.1 | 33.5 | 37.2 | 70.0 | 69.7 | 23.1 | 27.1 | 42.4 | 70.2 |
| GSR+Temp+BP | 57.0 | 64.0 | 54.8 | 5.2 | 55.4 | 67.0 | 34.2 | 54.4 | 5.2 | 66.4 |
| GSR+Temp+Q | 83.6 | 0.2 | 44.8 | 0.0 | 83.9 | 91.3 | 0.2 | 23.3 | 0.0 | 91.7 |
| GSR+IBI+Ox | 64.8 | 14.0 | 45.4 | 45.8 | 64.8 | 70.8 | 19.1 | 43.2 | 23.0 | 71.7 |
| GSR+IBI+BP | 60.2 | 34.4 | 52.8 | 29.8 | 61.5 | 64.3 | 32.2 | 43.7 | 29.5 | 64.8 |
| GSR+IBI+Q | 87.7 | 11.2 | 23.3 | 0.0 | 88.3 | 88.8 | 7.7 | 23.3 | 0.0 | 89.4 |
| GSR+Ox+BP | 71.3 | 40.7 | 37.1 | 5.2 | 71.2 | 81.9 | 23.1 | 4.1 | 29.8 | 82.1 |
| GSR+Ox+Q | 69.9 | 22.9 | 56.7 | 5.2 | 71.0 | 75.5 | 22.7 | 41.8 | 5.2 | 76.7 |
| GSR+BP+Q | 63.9 | 26.5 | 73.8 | 0.0 | 62.3 | 64.1 | 25.9 | 73.8 | 0.0 | 62.4 |
| Temp+IBI+Ox | 57.4 | 38.9 | 62.4 | 22.2 | 57.5 | 61.8 | 30.7 | 57.8 | 22.2 | 61.8 |
| Temp+IBI+BP | 55.8 | 71.6 | 51.2 | 5.2 | 53.9 | 55.3 | 70.0 | 54.0 | 5.2 | 53.0 |
| Temp+IBI+Q | 73.6 | 17.2 | 51.8 | 5.0 | 74.5 | 77.1 | 9.0 | 53.6 | 0.0 | 77.5 |
| Temp+Ox+BP | 70.6 | 34.5 | 44.2 | 5.4 | 72.1 | 72.3 | 33.9 | 40.4 | 5.2 | 73.7 |
| Temp+Ox+Q | 53.3 | 56.2 | 71.8 | 5.2 | 55.8 | 53.4 | 56.2 | 71.4 | 5.2 | 55.9 |
| Temp+BP+Q | 47.9 | 46.6 | 94.9 | 5.2 | 43.5 | 49.9 | 40.8 | 94.7 | 5.2 | 45.1 |
| IBI+Ox+BP | 65.0 | 59.1 | 37.5 | 5.2 | 66.1 | 64.1 | 60.8 | 38.4 | 5.2 | 65.0 |
| IBI+Ox+Q | 54.8 | 56.2 | 67.8 | 5.2 | 57.2 | 55.0 | 56.2 | 67.2 | 5.2 | 57.4 |
| IBI+BP+Q | 55.9 | 56.2 | 65.2 | 4.6 | 55.0 | 53.4 | 56.2 | 71.6 | 5.2 | 52.3 |
| Ox+BP+Q | 66.9 | 56.2 | 35.0 | 5.2 | 68.2 | 66.9 | 56.2 | 35.0 | 5.2 | 68.2 |

*FIG. 11*

Test Accuracy, FPR, FNRs, and F1 Score (All in %) for Two DNN Models Obtained for Feature Subsets from Four, Five or Six Data Categories

| Data Category | DNN Model 1 | | | | | DNN Model 2 | | | | |
|---|---|---|---|---|---|---|---|---|---|---|
| | Acc. | FPR | FNR(2) | FNR(3) | F1 Score | Acc. | FPR | FNR(2) | FNR(3) | F1 Score |
| GSR+Temp+IBI+Ox | 76.6 | 23.3 | 27.0 | 19.2 | 77.3 | 74.5 | 28.5 | 28.3 | 18.8 | 75.2 |
| GSR+Temp+IBI+BP | 62.5 | 27.1 | 53.4 | 29.2 | 62.4 | 73.3 | 13.6 | 44.0 | 19.8 | 73.4 |
| GSR+Temp+IBI+Q | 87.1 | 0.2 | 34.7 | 0.0 | 87.5 | 89.1 | 1.6 | 27.9 | 0.0 | 89.6 |
| GSR+Temp+Ox+BP | 77.6 | 24.2 | 34.7 | 5.2 | 77.8 | 93.6 | 1.7 | 11.4 | 5.2 | 93.7 |
| GSR+Temp+Ox+Q | 80.7 | 22.5 | 27.8 | 5.2 | 81.7 | 81.2 | 22.5 | 26.4 | 5.2 | 82.2 |
| GSR+Temp+BP+Q | 60.0 | 11.5 | 93.4 | 5.2 | 53.2 | 61.8 | 11.5 | 93.0 | 0.0 | 54.5 |
| GSR+IBI+Ox+BP | 75.0 | 23.3 | 42.6 | 5.2 | 76.1 | 76.8 | 24.2 | 37.0 | 5.2 | 77.8 |
| GSR+IBI+Ox+Q | 69.8 | 32.2 | 48.5 | 5.2 | 71.4 | 76.1 | 40.4 | 24.5 | 4.9 | 77.1 |
| GSR+IBI+BP+Q | 59.3 | 32.6 | 80.3 | 0.8 | 57.1 | 66.2 | 3.4 | 84.5 | 4.6 | 60.7 |
| GSR+Ox+BP+Q | 79.9 | 22.5 | 34.2 | 0.0 | 80.9 | 84.8 | 14.1 | 28.4 | 0.0 | 85.5 |
| Temp+IBI+Ox+BP | 59.2 | 25.9 | 58.9 | 5.2 | 61.1 | 66.9 | 53.8 | 37.2 | 5.2 | 67.9 |
| Temp+IBI+Ox+Q | 63.1 | 48.5 | 52.2 | 5.2 | 65.1 | 62.1 | 56.2 | 48.0 | 5.2 | 64.0 |
| Temp+IBI+BP+Q | 54.5 | 31.9 | 90.3 | 5.2 | 49.8 | 54.7 | 30.7 | 90.7 | 5.1 | 49.8 |
| Temp+Ox+BP+Q | 67.1 | 56.2 | 34.5 | 5.2 | 68.3 | 66.8 | 56.2 | 35.3 | 5.2 | 68.1 |
| IBI+Ox+BP+Q | 66.9 | 56.2 | 35.0 | 5.2 | 68.2 | 66.9 | 56.2 | 35.0 | 5.2 | 68.2 |
| GSR+Temp+IBI+Ox+BP | 77.1 | 29.1 | 31.8 | 5.2 | 78.2 | 83.3 | 34.2 | 10.3 | 5.2 | 83.7 |
| GSR+Temp+IBI+Ox+Q | 67.2 | 5.8 | 79.1 | 5.2 | 65.3 | 83.1 | 20.1 | 23.5 | 5.2 | 83.9 |
| GSR+Temp+IBI+BP+Q | 64.3 | 4.7 | 88.2 | 5.1 | 57.8 | 69.0 | 15.7 | 65.8 | 4.7 | 67.0 |
| GSR+Temp+Ox+BP+Q | 83.8 | 0.4 | 39.1 | 5.2 | 84.2 | 83.8 | 0.4 | 39.1 | 5.2 | 84.2 |
| GSR+IBI+Ox+BP+Q | 71.8 | 37.5 | 38.5 | 5.2 | 73.3 | 75.3 | 23.8 | 41.1 | 5.2 | 76.6 |
| Temp+IBI+Ox+BP+Q | 62.5 | 44.8 | 57.0 | 5.2 | 64.5 | 66.6 | 48.8 | 42.4 | 5.2 | 68.3 |
| GSR+Temp+IBI+Ox+BP+Q | 77.8 | 18.3 | 39.4 | 5.2 | 78.8 | 83.7 | 26.9 | 15.9 | 5.2 | 84.1 |

*FIG. 12*

Comparison of the Three DNN Models (All Performance Metrics in %) for Various Feature Sets

| Data Category | DNN Models 1 and 2 | | | | DNN Model 3 | | | | | |
|---|---|---|---|---|---|---|---|---|---|---|
| | Acc.(1) | Acc.(2) | FLOPs | #Param. | Acc. | FLOPs | #Param. | FPR | FNR(2) | FNR(3) | F1 Score |
| GSR+Ox+BP+Q | 79.9 | 84.8 | 136.4k | 68.5k | 98.1 | 19.5k | 10.0k | 0.8 | 4.5 | 0.0 | 98.2 |
| GSR+IBI+Q | 87.7 | 88.8 | 165.6k | 83.1k | 91.5 | 39.5k | 20.0k | 1.3 | 21.9 | 0.0 | 91.9 |
| GSR+Q | 89.1 | 89.2 | 134.9k | 67.7k | 91.3 | 9.5k | 5.0k | 0.2 | 23.2 | 0.0 | 91.7 |
| GSR+Temp+Q | 83.6 | 91.3 | 165.6k | 83.1k | 91.3 | 151.5k | 76.0k | 0.2 | 23.3 | 0.0 | 91.7 |
| GSR+Temp+IBI+Q | 87.1 | 89.1 | 196.3k | 98.4k | 90.7 | 19.5k | 10.0k | 0.2 | 20.7 | 5.2 | 91.0 |
| GSR+Temp+Ox+Q | 80.7 | 81.2 | 166.1k | 83.3k | 87.7 | 119.5k | 60.0k | 0.3 | 28.7 | 5.2 | 88.1 |
| GSR-Temp-IBI-OX-Q | 67.2 | 83.1 | 196.8k | 98.7k | 86.4 | 59.5k | 30.0k | 11.3 | 22.6 | 5.2 | 87.0 |
| GSR+Temp+IBI+Ox+BP | 77.1 | 83.3 | 192.2k | 96.4k | 84.6 | 59.5k | 30.0k | 29.5 | 11.2 | 5.2 | 85.1 |
| GSR+Ox+BP | 71.3 | 81.9 | 130.8k | 65.7k | 82.4 | 89.5k | 45.0k | 23.8 | 2.1 | 29.8 | 82.5 |
| GSR+Temp+Ox+BP | 77.6 | 93.6 | 161.5k | 81.0k | 82.3 | 129.5k | 65.0k | 25.2 | 21.0 | 5.2 | 82.8 |
| IBI+Q | 80.9 | 80.9 | 134.9k | 67.7k | 81.7 | 19.5k | 10.0k | 29.3 | 23.3 | 0.0 | 82.5 |

*FIG. 13*

SYSTEM AND METHOD FOR TESTING FOR SARS-COV-2/COVID-19 BASED ON WEARABLE MEDICAL SENSORS AND NEURAL NETWORKS

CROSS-REFERENCE TO RELATED APPLICATIONS

This application claims priority to provisional applications 63/022,997 and 63/053,912, filed May 11, 2020 and Jul. 20, 2020, respectively, which are herein incorporated by reference in their entirety.

STATEMENT REGARDING FEDERALLY SPONSORED RESEARCH OR DEVELOPMENT

This invention was made with government support under Grant No. CNS-1907381 awarded by the National Science Foundation. The government has certain rights in the invention.

FIELD OF THE INVENTION

The present invention relates generally to wearable medical sensors and neural networks and, more particularly, to a system and method for detecting coronavirus based on wearable medical sensor data and neural network processing that bypasses feature extraction.

BACKGROUND OF THE INVENTION

SARS-COV-2, also known as novel coronavirus, emerged in China and soon after spread across the globe. The World Health Organization (WHO) named the resultant disease COVID-19. COVID-19 was declared a pandemic on Mar. 11, 2020. In its early stages, the symptoms of COVID-19 include fever, cough, fatigue, and myalgia. However, in more serious cases, it can lead to shortness of breath, pneumonia, severe acute respiratory disorder, heart problems, and even death. It is of paramount importance to detect which individuals are infected at as early a stage as possible in order to limit the spread of disease through quarantine and contact tracing. In response to COVID-19, governments around the world have issued social distancing and self-isolation orders. This has led to a significant increase in unemployment across diverse economic sectors. As a result, COVID-19 has triggered an economic recession in a large number of countries.

Reverse Transcription-Polymerase Chain Reaction (RTPCR) is currently the gold standard for SARS-CoV-2 detection. This test is based on viral nucleic acid detection in sputum or nasopharyngeal swab. Although it has high specificity, it has several drawbacks. The RT-PCR test is invasive and uncomfortable, and non-reusable testing kits have led to significant supply chain deficiencies. SARS-CoV-2 infection can also be assessed with an antibody test. However, antibody titers are only detectable from the second week of illness onwards and persist for an uncertain length of time. The antibody test is also invasive, requiring venipuncture which, in combination with a several-day processing time, makes it less ideal for rapid mass screening. In the current economic and social situation, there is a great need for an alternative SARS-CoV-2/COVID-19 detection method that is easily accessible to the public for repeated testing with high accuracy.

To address the above issues, researchers have begun to explore the use of artificial intelligence (AI) algorithms to detect COVID-19. Initial work concentrated on CT scans and X-ray images. These methods often rely on transfer learning of a convolutional neural network (CNN) architecture, pre-trained on large image datasets, on a smaller COVID-19 image dataset. However, such an image-based AI approach faces several challenges that include lack of large datasets and inapplicability outside the clinic or hospital. In addition, other work shows that it is difficult to distinguish COVID-19 pneumonia from influenza virus pneumonia in a clinical setting using CT scans. Thus, the work in this area is not mature yet.

CORD-19 is an assembly of 59000 scholarly articles on COVID-19. It can be used with natural language processing methods to distill useful information on COVID-19-related topics.

AI4COVID-19 performs a preliminary diagnosis of COVID-19 through cough sample recordings with a smartphone application. However, since coughing is a common symptom of two dozen non-COVID-19 medical conditions, this is an extremely difficult task. Nonetheless, AI4COVID-19 shows promising results and opens the door for COVID-19 diagnosis through a smartphone.

The emergence of wearable medical sensors (WMSs) offers a promising way to tackle these challenges. WMSs can continuously sense physiological signals throughout the day. Hence, they enable constant monitoring of a user's health status. Training AI algorithms with data produced by WMSs can enable pervasive health condition tracking and disease onset detection. This approach exploits the knowledge distillation capability of machine learning algorithms to directly extract information from physiological signals. Thus, it is not limited to disease detection in the clinical scenarios.

SUMMARY OF THE INVENTION

According to various embodiments, a machine-learning based system for coronavirus detection is disclosed. The system includes one or more processors configured to interact with a plurality of wearable medical sensors (WMSs). The processors are configured to receive physiological data from the WMSs and questionnaire data from a user interface. The processors are further configured to train at least one neural network based on raw physiological data and questionnaire data augmented with synthetic data and subjected to a grow-and-prune paradigm to generate at least one coronavirus inference model. The processors are also configured to output a coronavirus-based decision by inputting the received physiological data and questionnaire data into the generated coronavirus inference model.

According to various embodiments, a machine-learning based method for coronavirus detection based on one or more processors configured to interact with a plurality of wearable medical sensors (WMSs) is disclosed. The method includes receiving physiological data from the WMSs and questionnaire data from a user interface. The method further includes training at least one neural network based on raw physiological data and questionnaire data augmented with synthetic data and subjected to a grow-and-prune paradigm to generate at least one coronavirus inference model. The method also includes outputting a coronavirus-based decision by inputting the received physiological data and questionnaire data into the generated coronavirus inference model.

According to various embodiments, a non-transitory computer-readable medium having stored thereon a computer program for execution by a processor configured to perform a machine-learning based method for coronavirus detection is disclosed. The method includes receiving physiological data from the WMSs and questionnaire data from a user interface. The method further includes training at least one neural network based on raw physiological data and questionnaire data augmented with synthetic data and subjected to a grow-and-prune paradigm to generate at least one coronavirus inference model. The method also includes outputting a coronavirus-based decision by inputting the received physiological data and questionnaire data into the generated coronavirus inference model.

According to various embodiments, a machine-learning based system for coronavirus detection is disclosed. The system includes one or more processors configured to interact with a plurality of wearable medical sensors (WMSs). The processors are configured to receive physiological data from the WMSs and questionnaire data from a user interface. The processors are further configured to train at least one neural network based on raw physiological data and questionnaire data augmented with synthetic data to generate at least one coronavirus inference model. The processors are also configured to output a coronavirus-based decision by inputting the received physiological data and questionnaire data into the generated coronavirus inference model.

Various other features and advantages will be made apparent from the following detailed description and the drawings.

BRIEF DESCRIPTION OF THE DRAWINGS

In order for the advantages of the invention to be readily understood, a more particular description of the invention briefly described above will be rendered by reference to specific embodiments that are illustrated in the appended drawings. Understanding that these drawings depict only exemplary embodiments of the invention and are not, therefore, to be considered to be limiting its scope, the invention will be described and explained with additional specificity and detail through the use of the accompanying drawings, in which:

FIG. 5 depicts a connection growth methodology according to an embodiment of the present invention;

FIG. 6 depicts a connection pruning methodology according to an embodiment of the present invention;

FIG. 7 depicts a neuron growth methodology according to an embodiment of the present invention;

FIG. 8 depicts a table of data types collected in a CovidDeep framework according to an embodiment of the present invention;

FIG. 9 depicts a table of a confusion matrix for the most accurate three-way classification model according to an embodiment of the present invention;

FIG. 10 depicts a table of test accuracy, FPR, FNRs, and F1 score for three DNN models obtained for the most accurate case according to an embodiment of the present invention;

FIG. 11 depicts a table of test accuracy, FPR, FNRs, and F1 score for two DNN models obtained for feature subsets from one, two, or three data categories according to an embodiment of the present invention;

FIG. 12 depicts a table of test accuracy, FPR, FNRs, and F1 score for two DNN models obtained for feature subsets from four, five, or six data categories according to an embodiment of the present invention; and FIG. 13 depicts a table of a comparison of the three DNN models for various feature sets according to an embodiment of the present invention.

DETAILED DESCRIPTION OF THE INVENTION

Figure 1:
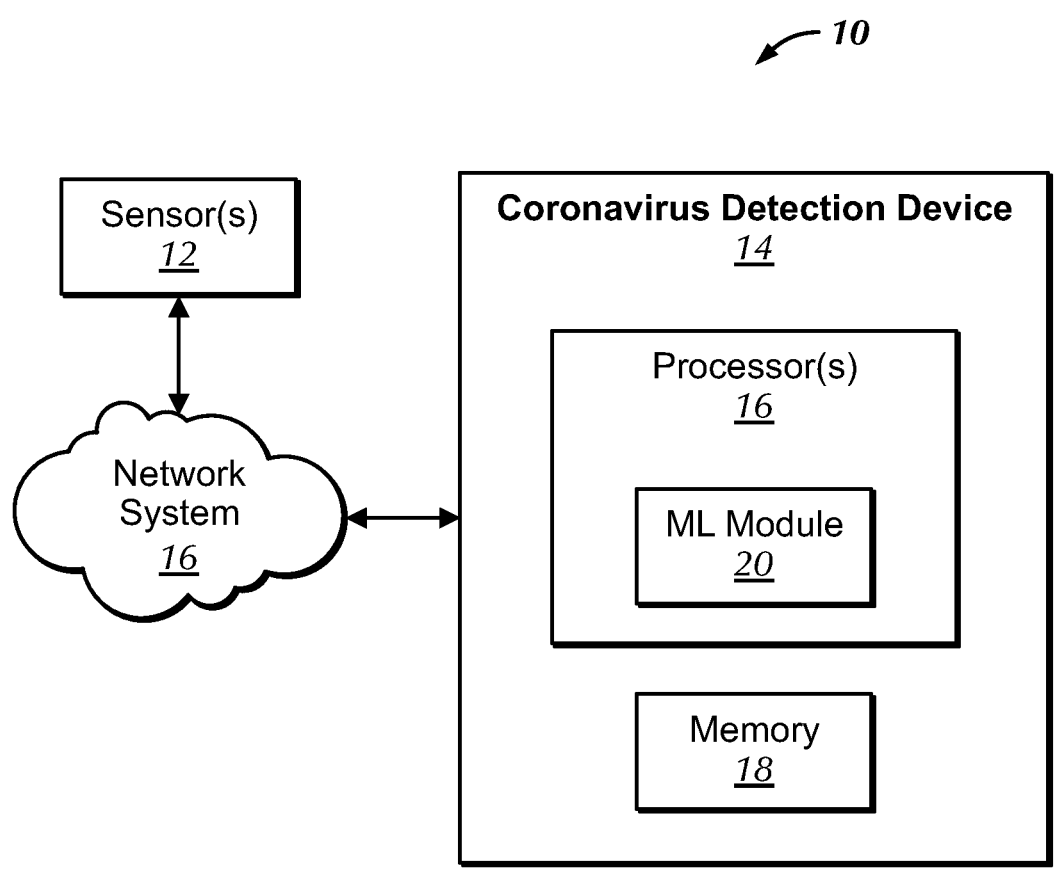
FIG. 1 depicts a block diagram of a system for implementing a CovidDeep framework according to an embodiment of the present invention.

The novel coronavirus (SARS-CoV-2) has led to a pandemic. Because of its highly contagious nature, it has spread rapidly, resulting in major disruption to public health and a huge loss of human life. In addition, due to governmental orders for isolation and social distancing, it has also had a severe negative impact on the world economy. As a result, it is widely recognized that widespread testing is key to containing the spread of the disease and opening up the economy. However, the current testing regime based on Reverse Transcription-Polymerase Chain Reaction for SARS-CoV-2 has been unable to keep up with testing demands and also suffers from a relatively low positive detection rate in the early stages of the resultant disease, called COVID-19. Hence, there is a need for an alternative approach for repeated large-scale testing of SARS-CoV-2/COVID-19. The emergence of wearable medical sensors (WMSs) and deep neural networks (DNNs) points to a promising approach to address this challenge. WMSs enable continuous and user-transparent monitoring of physiological signals. However, disease detection based on WMSs/DNNs and their deployment on resource-constrained edge devices remain challenging problems.

To address these problems, generally disclosed herein are embodiments for a framework called CovidDeep that combines efficient DNNs with commercially available WMSs for pervasive testing of the coronavirus in both the asymptomatic and symptomatic cases. CovidDeep does not depend on manual feature extraction. It directly operates on WMS data and some easy-to-answer questions in a questionnaire whose answers can be obtained through a smartphone application. Data was collected from 87 individuals, spanning three cohorts that include healthy, asymptomatic (but SARS-CoV-2-positive) as well as symptomatic COVID-19 patients. DNNs were trained on various subsets of the features automatically extracted from six WMS and questionnaire categories to perform ablation studies to determine which subsets are most efficacious in terms of test accuracy for a three-way classification. The highest test accuracy obtained was 98.1%.

Since data collection was limited to only 87 individuals (because of the intensive nature of data collection), experiments were performed that augmented the real training dataset with a synthetic training dataset drawn from the same probability distribution. The synthetic dataset was used to impose a prior on the DNN weights. Furthermore, a grow-and-prune DNN synthesis paradigm was leveraged to simultaneously learn both the weights and the network architecture. Addition of synthetic data and use of growand-prune synthesis boosted the accuracy of the various DNNs further and simultaneously reduced their size and floating-point operations. This makes the CovidDeep DNNs both accurate and efficient, in terms of memory requirements and computations. The resultant DNNs can be easily deployed on edge devices, e.g., smartwatch or smartphone, which has the added benefit of preserving patient privacy.

Synthesizing and Training Efficient DNN Architectures

This section involves methods for synthesizing and training efficient DNN architectures.

One approach is based on the use of efficient building blocks. Using such blocks results in compact networks and significantly reduces the computational costs and storage needs. For example, inverted residual blocks used in MobileNetV2 reduce the number of parameters and the floating-point operations (FLOPs) greatly. In addition, spatial convolution is one of the most computationally expensive operations in CNN architectures. To address this issue, ShuffleNet-v2 uses the depth-wise separable convolutions and channel-shuffling operations. Furthermore, Shift addresses this problem by using shift-based modules that combine shifts and point-wise convolutions. Neural architecture search (NAS) is also used to automatically generate compact architectures. For example, FBNetV2 uses differentiable NAS approach to synthesize compact CNN architectures. Efficient performance predictors, e.g., for accuracy, latency, and energy, are also used to accelerate the DNN search process. FBNetV3 considers the training recipe (i.e., training hyperparameters) in the NAS as well, leading to finding higher accuracy-recipe combinations.

In addition, DNN compression methods can remove redundancy in the DNN models. Network pruning uses a pruning methodology to remove redundancy from both CNN and multilayer-perceptron architectures. ESE shows the pruning methods are also helpful in removing redundancy in recurrent neural networks. Network growth can be combined with pruning to generate efficient CNNs and long short-term memories. SCANN combines feature dimensionality reduction with grow-and-prune synthesis to generate very compact models that can be easily deployed on edge devices and Internet-of-Things (IoT) sensors.

Orthogonal to the above, low-bit quantization of DNN weights can also be used to reduce computations in a network with little to no accuracy drop.

System Overview

FIG. 1 depicts a system 10 configured to implement machine learning based coronavirus detection from WMS data. The system 10 includes one or more wearable medical sensors (WMSs) 12. The WMSs 12 may be connected to a coronavirus detection device 14 via a network system 16. The WMSs 12 may also be integrated into the device 14, in which case a network system 16 is not required. The device 14 may be implemented in a variety of configurations including general computing devices such as but not limited to desktop computers, laptop computers, tablets, network appliances, and the like. The device 14 may also be implemented as a mobile device such as but not limited to a mobile phone, smart phone, smart watch, or tablet computer. Where the WMSs 12 are integrated into the device 14, the device 14 may be implemented as one or more IoT sensors.

The device 14 includes one or more processors 16 such as but not limited to a central processing unit (CPU), a graphics processing unit (GPU), or a field programmable gate array (FPGA) for performing specific functions and memory 18 for storing those functions. The processor 16 includes a machine learning (ML) module 20 for detecting coronavirus. The ML module 20 methodology will be described in greater detail below. It is also to be noted the training process for the ML module 20 may be implemented in a number of configurations with a variety of processors (including but not limited to central processing units (CPUs), graphics processing units (GPUs), and field programmable gate arrays (FPGAs)), such as servers, desktop computers, laptop computers, tablets, and the like.

The network system 16 may be implemented as a single network or a combination of multiple networks. Network system 16 may include but is not limited to wireless telecommunications networks, WiFi, Bluetooth, Zigbee, or other communications networks. Network system 16 may be a wired network as well.

Methodology

This section describes the CovidDeep framework. First, an overview of the entire framework is disclosed. Then, the DNN architecture that is used in CovidDeep for inference is explained. It is also described how synthetic data generation can be used to impose a prior on the DNN weights and then how the DNN grow-and-prune synthesis paradigm is used to boost the test accuracy further and ensure computational efficiency of the model.

Framework Overview

Figure 2:
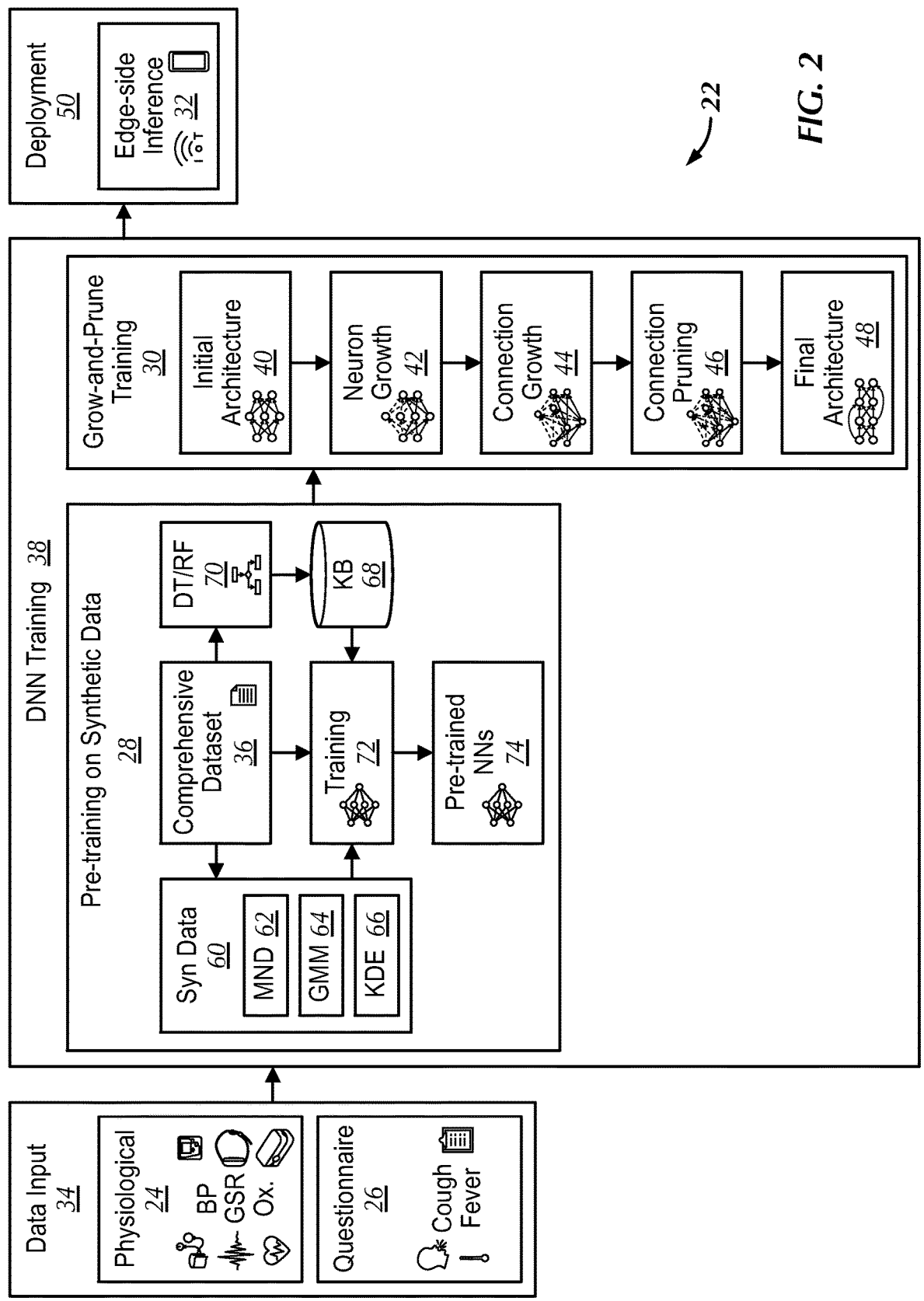
FIG. 2 depicts a schematic diagram of a CovidDeep framework according to an embodiment of the present invention.

The CovidDeep framework 22 is shown in FIG. 2. CovidDeep 22 obtains data from two different sources: physiological signals 24 and a questionnaire 26. It has two flows: one that does not use synthetic data and another one that does. When synthetic data are not used, the framework 22 just uses the real dataset divided into three categories: training, validation, and test. The framework 22 trains the DNNs with the training dataset and picks the best one for the given set of features based on the validation dataset, and finally tests this DNN on the test dataset to obtain the test accuracy.

However, when the real training dataset size is small, it is often advantageous to draw a synthetic dataset from the same probability distribution. CovidDeep 22 uses synthetic data generation methods to increase the dataset size and use such data to pre-train the DNN architecture 28. Then, it uses grow-and-prune synthesis 30 to generate inference models that are both accurate and computationally efficient. The models generated by CovidDeep 22 are efficient enough to be deployed on the edge 32, e.g., the smartphone or smartwatch, for SARS-CoV-2/COVID-19 inference.

Data input 34: As mentioned above, physiological signals 24 and a questionnaire 26 are the two sources of data input to the model. The physiological signals 24 can be derived from WMSs embedded in a smartwatch as well as a discrete pulse oximeter and blood pressure monitor. These signals 24 can be easily obtained in a non-invasive, passive, and user-transparent manner. The list of these signals 24 includes Galvanic skin response (GSR) and inter-beat interval (IBI) that indicates the heart rate, skin temperature, oxygen saturation, and blood pressure (systolic and diastolic). In the questionnaire 26, the following yes/no questions are asked: immune-compromised, chronic lung disease, cough, shortness of breath, chills, fever, muscle pain, headache, sore throat, smell-taste loss, and diarrhea. Data can also be collected on age, gender, weight, height, and smoking/drinking (yes/no), but this data were not found to be useful either because of overfitting or being unrepresentative. The questionnaire data 26 can be obtained from a user interface on an application on a smart device or asked by a doctor and input into a smart device as nonlimiting examples. All the relevant data sources are aggregated into a comprehensive data input 36 for further processing.

Model training 38: CovidDeep 22 uses different types of DNN models: (i) those trained on the raw data only, (ii)

those trained on raw data augmented with synthetic data to boost accuracy, and (iii) those subjected to grow-and-prune synthesis for both boosting accuracy further and reducing model size. The first type of DNN model uses a few hidden layers. The second type of DNN model is trained based on a DNN synthesis framework called TUTOR and is suitable for settings where data availability is limited. It provides the DNN with a suitable inductive bias. The third type of DNN model is based on the grow-and-prune DNN synthesis paradigm and employs three architecture-changing operations. From an initial architecture 40, it iteratively employs neuron growth 42, connection growth 44, and connection pruning 46 until a final architecture 48 is achieved. These operations have been shown to yield DNNs that are both accurate and efficient.

Model inference 50: CovidDeep 22 enables the users to have SARS-CoV-2/COVID-19 detection decision on their edge device 32 on demand.

Model Architecture

Figure 3:
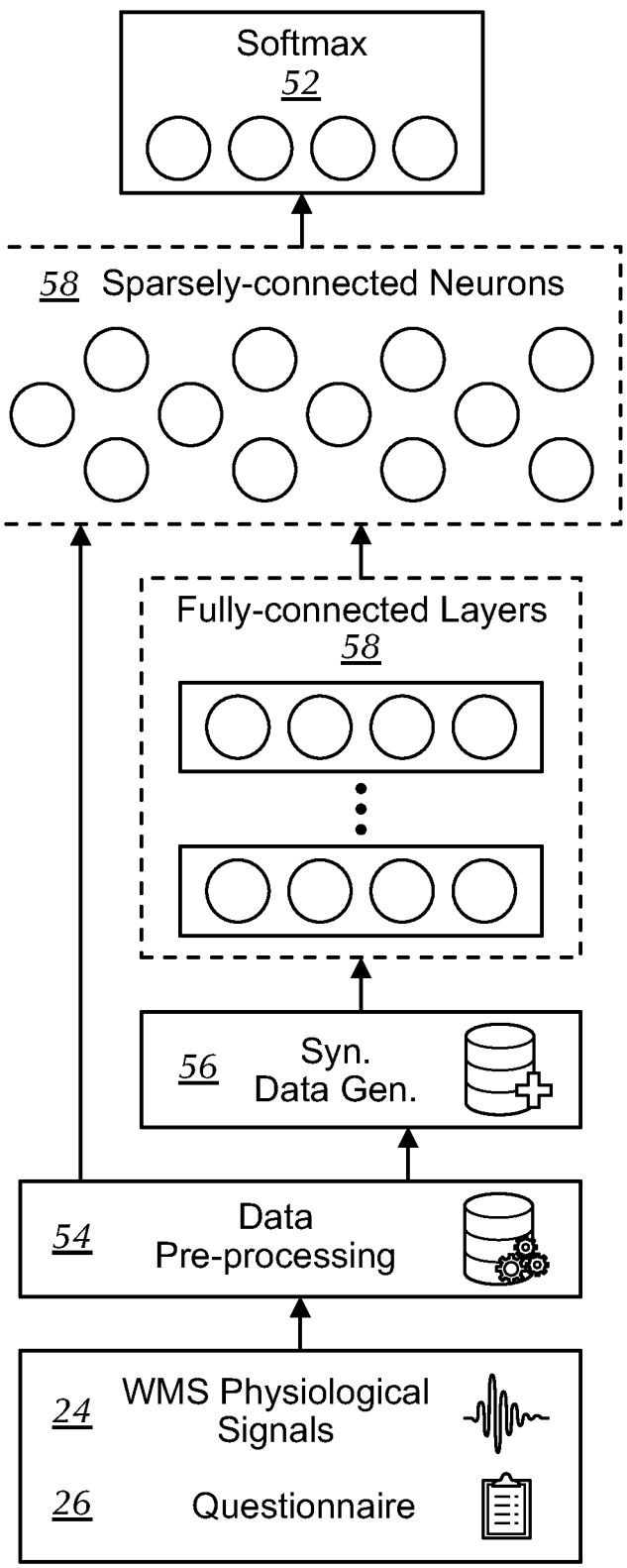
FIG. 3 depicts an illustration of a CovidDeep processing pipeline to generate predictions from data inputs according to an embodiment of the present invention.

FIG. 3 shows the processing pipeline of the CovidDeep framework 22. The architecture takes the data inputs 24, 26 (shown at the bottom) and generates a prediction, i.e., the detection decision, 52 (shown at the top). The pipeline includes four steps: data pre-processing 54, synthetic data generation and architecture pre-training 56, grow-and-prune synthesis 58, and output generation 52 through softmax.

In the data pre-processing stage 54, data normalization and data alignment/aggregation are done.

Data normalization is aimed at changing feature values to a common scale. While data normalization is not always required, it is highly beneficial in the case of datasets that have features with highly different ranges. It leads to better noise tolerance and improvement in model accuracy. Data normalization can be done in several ways, such as min-max scaling and standardization. Here, min-max scaling is used to map each data input to the [0,1] interval. Scaling can be done as follows:

$$x_{scaled} = \frac{x - \min(x)}{\max(x) - \min(x)} \quad (1)$$

For data alignment/aggregation, the data from different WMSs may have different start times and frequencies. In order to merge them into a dataset, the data streams should be synchronized based on their timestamps. The answers to the questions in the questionnaire are also added to the final dataset.

Figure 4:
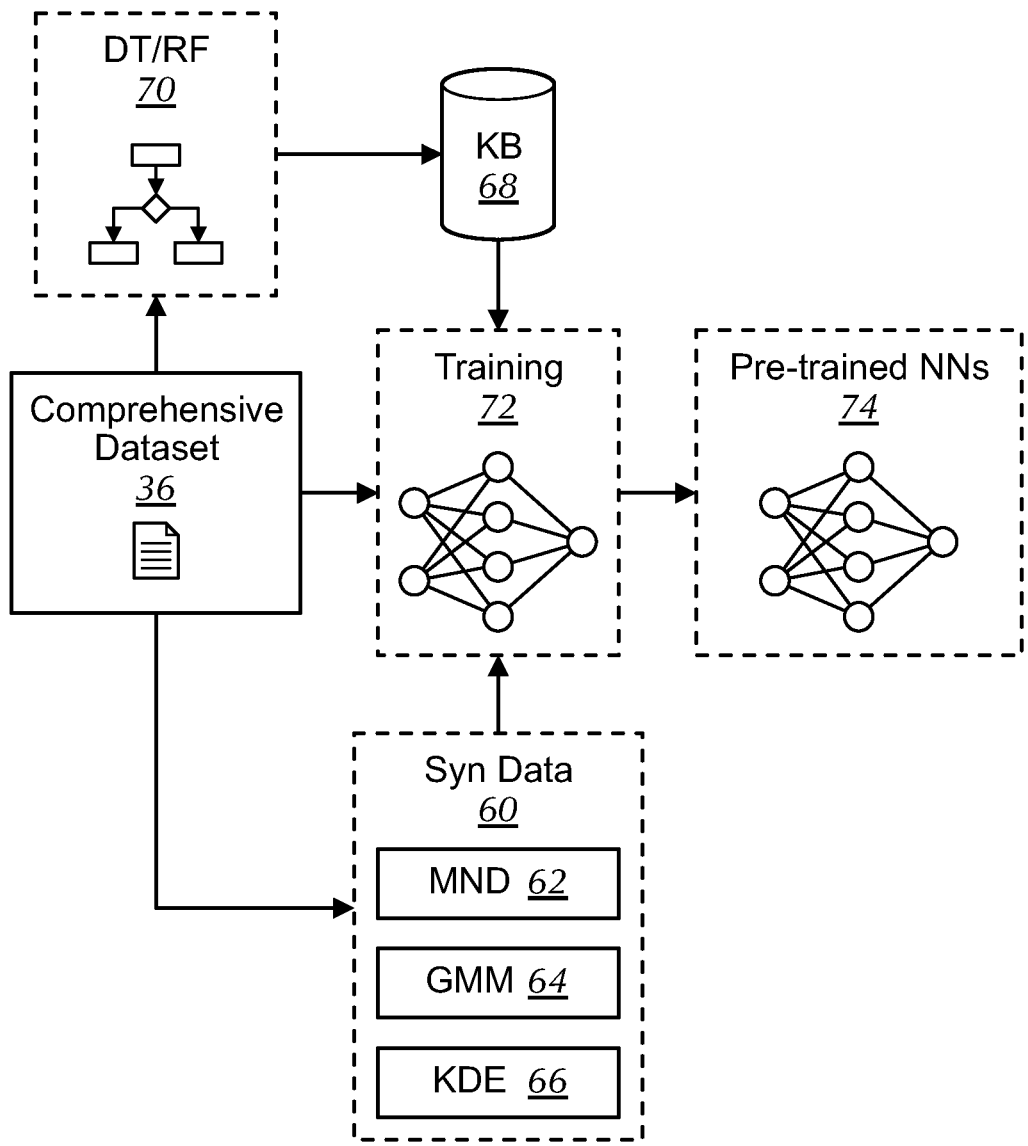
FIG. 4 depicts a schematic diagram for pretraining of a DNN model with a synthetic dataset according to an embodiment of the present invention.

Synthetic data generation 56: The training dataset 36 generated in the above manner is next used to generate a synthetic dataset 60 that is used to pre-train the DNN. These synthetic data and pre-training steps are based on the TUTOR framework, described in detail in Hassantabar et al., "TUTOR: Training neural networks using decision rules as model priors," arXiv preprint arXiv:2010.05429, 2020, which is herein incorporated by reference in its entirety. The schematic diagram of the training scheme based on synthetic data is shown in FIG. 4. The synthetic dataset 60 is generated in three different ways in TUTOR.

(1) Using multi-variate Normal distribution (MND) 62: In this approach, the real training dataset, i.e., the one obtained as a fraction of the data obtained from the WMSs and questionnaire, is modeled as a normal distribution to generate the synthetic data 60.

(2) Using Gaussian mixture model (GMM) 64: This approach uses a multi-dimensional GMM to model the data distribution. The optimal number of GMM components is obtained with the help of a validation dataset. Subsequently, the synthetic dataset 60 is generated from this GMM.

(3) Using kernel density estimation (KDE) 66: This approach uses non-parametric density estimation to estimate the probability distribution as a sum of many kernels. In the implementation here, KDE is based on the Gaussian kernel function. The synthetic data 60 are generated based on samples generated from this model.

Building a knowledge base (KB) 68: After generation of the synthetic data 60, the data points need to be labeled. To this end, a KB 68 is built from the real training dataset 36. Decision tree (DT) and random forest (RF) 70 are two machine learning methods that are inherently rule-based. In fact, each decision path in a decision tree, from the root to a leaf, can be thought of as a rule. Therefore, it is aimed to identify the set of rules that best describes the data. We use such a model as a KB 68 to label the generated synthetic dataset 60.

Training with synthetic data 72: The labeled synthetic data 60 is used to impose a prior on the DNN weights. To accomplish this, the DNN model is pre-trained by using the generated synthetic dataset 60. This outputs pre-trained NNs 74, which provides the framework with an appropriate inductive bias and helps the framework to "get underway." This helps improve accuracy when data availability is limited.

Grow-and-Prune Synthesis of the DNN

This section describes the grow-and-prune synthesis paradigm, which is presented in Hassantabar et al., "SCANN: Synthesis of compact and accurate neural networks," arXiv preprint arXiv.1904.09090, 2019, which is herein incorporated by reference in its entirety. This approach allows the depth of the DNN to grow during synthesis. Thus, a hidden neuron can receive inputs from any neuron activated before it (including input neurons) and can feed its output to any neuron activated after it (including output neurons). As a result, the depth of the model is determined based on how the hidden neurons are connected, enabling the depth to be changed during training. Three architecture-changing operations are used in the grow-and-prune synthesis process.

Connection growth 44: This activates the dormant connections in the network. The weights of the added connections are set to 0 and trained later. Two different methods are used for connection growth:

(1) Gradient-based growth: This approach was first introduced in Dai et al., "NeST: A neural network synthesis tool based on a grow-and-prune paradigm," *IEEE Trans. Computers*, vol. 68, no. 10, pp. 1487-1497, October 2019, which is herein incorporated by reference in its entirety. The algorithm in FIG. 5 shows the process of gradient-based growth. Each weight matrix has a corresponding binary mask of the same size. This mask is used to disregard the inactive connections. The algorithm adds connections to reduce the loss function L significantly. To this end, the gradients of all the dormant connections are evaluated and their effectiveness ranked based on this metric. During a training epoch, the gradients of all the weight matrices for all the data mini-batches are captured in the back-propagation step. An inactive connection is activated if its gradient magnitude is large relative to the gradients in its associated layer, for instance being in the top few percentile.

(2) Full growth: This connection growth restores all the dormant connections in the network to make the DNN fully-connected.

Connection pruning 46: Connection pruning deactivates the connections whose weights are smaller than a specified threshold that should be close to 0. The algorithm in FIG. 6 shows this process.

Neuron growth 42: This step adds neurons to the network and thus increases network size. This is done by duplicating existing neurons in the architecture. To break the symmetry, random noise is added to the weights of all the connections related to the newly added neurons. The neurons to be duplicated are either selected randomly or based on higher activation values. The process is explained in the algorithm in FIG. 7.

Connection pruning 46 is applied after neuron growth 42 and connection growth 44 in each iteration. Grow-and-prune synthesis starts from a fully connected architecture (mask values set to 1) and runs for a pre-defined number of iterations. Finally, the architecture that performs the best (i.e., has the highest accuracy) on the validation dataset is chosen.

Implementation Details

The section explains how the data were obtained from 87 individuals and how various datasets were prepared from the data. This section also provides implementation details of the CovidDeep DNN model.

Data Collection and Preparation

Physiological signals and questionnaire data was collected with Institutional Research Board (IRB) approval at San Matteo Hospital in Pavia, Italy. 30 individuals were healthy (referred to as Cohort 1) and the remaining were SARS-CoV-2-positive with varying levels of disease severity. The SARS-CoV-2-positive cases were categorized into two other cohorts: asymptomatic (Cohort 2 with 27 individuals) and symptomatic (Cohort 3 with 30 individuals). Distinguishing among these cohorts is important to ascertain who may be spreading the virus unknowingly and to determine whether medical support is needed for symptomatic individuals. Hence, DNN models are trained that can perform three-way classification.

To collect the physiological signals, commercially available devices were used: Empatica E4 smartwatch (sensors found useful were GSR, IBI, and skin temperature), a pulse oximeter, and a blood pressure monitor. Alongside the physiological signals, a questionnaire was employed to collect information about possible COVID-19-related symptoms from all the individuals. Data was also collected about age, gender, weight, height, and smoking/drinking (yes/no), but did not rely on these features as they were not necessarily representative of the larger population. The table in FIG. 8 shows all the data types that were found to be useful. The smartwatch data capture the physiological state of the user. GSR measures continuous variations in the electrical characteristics of the skin, such as conductance, which can be caused by variations in body sweat. IBI correlates with cardiac health. Furthermore, skin acts as a medium for insulation, sweat, and control of blood flow. Although it is not a clear indicator of internal body temperature, skin temperature helps assess skin health. The pulse oximeter indirectly measures blood oxygen saturation. It is a comfortable and painless way of measuring how well oxygen is being sent to parts of the body furthest from the heart, such as the arms and legs. Blood pressure exposes various underlying health problems. Last, but not the least, the questionnaire elicits information that may help improve COVID-19 detection accuracy. From all these sources of data, various subsets are derived as datasets for use in the CovidDeep framework to see which data features are the most beneficial to obtaining a high detection accuracy. In addition, the various sensor subsets have different costs. Hence, the results also let one take test accuracy vs. cost into consideration.

Before data collection commences, the participants are informed about the procedure. Some relevant information and COVID-19-related symptoms are then collected in response to a questionnaire. The pulse oximeter is placed on the index finger of the user for blood oxygen measurement. The systolic/diastolic blood pressure measurements are also obtained. The smartwatch is placed on the participant's wrist. Data collection lasts for at most one hour for each participant, during which time sensor data is collected from the smartwatch. The data is streamed from the smartwatch to the smartphone over Bluetooth in real-time using a smartphone application. This application collects the data and performs basic validation to ensure data integrity.

Next, the raw data is pre-processed to generate a comprehensive dataset. To this end, the WMS data streams are first synchronized. The data streams are then divided into 15-second data windows. The participants are then split into three different sets of training, validation, and test. The training set contains data from 52 individuals, approximately 60% of all the participants. Among the 52 individuals represented in the training set, 18 are healthy, 16 are asymptomatic (but virus-positive), and 18 are symptomatic (and virus-positive). The validation set includes data from 17 individuals, approximately 20% of all the participants, with 6, 5, and 6 individuals from Cohorts 1, 2, and 3, respectively. The test set contains data from 18 individuals, approximately 20% of all the participants, with 6 individuals from each of the three cohorts. This data partitioning ensures that all the data collected from any individual are limited to just one of the three sets. Furthermore, the data instances extracted from each individual have no time overlap. In addition, to conduct ablation studies to gauge the impact of different data streams, different datasets are created, with various subsets of all the features.

Model Implementation

The CovidDeep framework was implemented in PyTorch. DNN training is performed on the Nvidia Tesla P100 data center accelerator, with 16 GB of memory. cuDNN library is used to accelerate GPU processing. Next, the details of the implemented DNN architectures trained on the different datasets are given.

Various DNNs (with different numbers of layers and different numbers of neurons per layer) are trained and their performance is verified on the validation dataset. In general, a four-layer architecture with 256, 128, 128, and 3 neurons, respectively, performs the best. The number of neurons in the input layer depends on which subset of features is selected for training the DNN. In the case of the full dataset, the input layer has 194 neurons, which indicates the dataset dimension. The features of the dataset from the 15 s data window were obtained as follows. Sensor data collected from the smartwatch in the data window include 180 signal readings, hence, 180 features, from the three data streams running at 4 Hz. 11 features are derived from the 11 questionnaire questions. Finally, the pulse oximeter oxygen saturation measurement and systolic/diastolic blood pressure measurements are appended to obtain a feature vector of length 194.

Leaky ReLU is used as the nonlinear activation function in all the DNN layers. As explained prior, three DNNs are generated for each dataset: (i) DNN trained on the real training dataset, (ii) DNN pre-trained on the synthetic dataset and then trained on the real training dataset, and (iii) DNN synthesized and trained with the grow-and-prune synthesis paradigm.

Network Training

The stochastic gradient descent optimizer is used for DNN training, with a learning rate of 5e−3 and batch size of 256. 100000 synthetic data instances are used to pre-train the network architecture. Moreover, in the grow-and-prune synthesis phase, the network is trained for 20 epochs each time the architecture changes. Network-changing operations are applied over five iterations. In this step, pruning is used to achieve a pre-defined number of connections in the network, chosen based on performance on the validation set.

Experimental Results

This section analyzes the performance of CovidDeep DNN models. Three-way classification is targeted among the three cohorts described earlier. In addition, an ablation study is performed to analyze the impact of different subsets of features as well as different steps of CovidDeep DNN synthesis.

The CovidDeep DNN models are evaluated with four different metrics: test accuracy, false positive rate (FPR), false negative rate (FNR), and F1 score. These terms are based on the following:

True positive (negative): SARS-CoV-2/COVID-19 (healthy) data instances classified as SARS-CoV-2/COVID-19 (healthy).

False positive (negative): healthy (SARS-CoV-2/COVID-19) data instances classified as SARS-CoV-2/COVID-19 (healthy).

These metrics evaluate the model performance from different perspectives. Test accuracy evaluates its overall prediction power. It is simply the ratio of all the correct predictions on the test data instances and the total number of such instances. The FPR is defined as the ratio of the number of negative, i.e., healthy, instances wrongly categorized as positive (false positives) and the total number of actual negative instances. The FNR is the ratio of positives that yield different test outcomes. Thus, there is an FNR for both Cohorts 2 and 3. Because of the three-way classification, the F1 score reported is the Macro F1 score.

Model Performance Evaluation

The highest test accuracy was obtained with a DNN model trained with the grow-and-prune synthesis paradigm on the dataset that contained features from four categories: GSR, pulse oximeter (Ox), blood pressure (BP), and questionnaire (Q). The table in FIG. 9 shows the confusion matrix for three-way classification among the three cohorts: Cohort 1 (healthy), Cohort 2 (asymptomatic-positive), Cohort 3 (symptomatic-positive), denoted as C1, C2, and C3, respectively. CovidDeep DNN achieves a test accuracy of 98.1%. The model achieves an FPR of only 0.8%. The low FPR means that the model does not raise many false alarms. It results in a 4.5% FNR for Cohort 2 and a 0.0% FNR for Cohort 3, denoted as FNR(2) and FNR(3), respectively (each FNR refers to the ratio of the number of false predictions for that cohort divided by the total number of data instances of that type). The low FNRs demonstrate the ability of the DNN model to not miss virus-positive cases. Moreover, the Macro F1 score of the DNN model is also high: 98.2%.

Next, the three DNN models are compared, trained on the real training dataset, with the aid of synthetic data, and with the aid of grow-and-prune synthesis, for the most accurate case in the table in FIG. 10. From this comparison, it is shown that the use of synthetic data and then grow-and-prune synthesis can boost the test accuracy compared to the DNN model trained on just the real dataset. In addition, improvements are seen in the FPR and FNR values. The F1 score also follows the same trend, increasing with the use of synthetic data, and even more with the use of grow-and-prune synthesis.

Ablation Studies

This section reports the results on various ablation studies. First, DNN models trained on features obtained from subsets of the six data categories (five sensors and the questionnaire) are considered. This helps to understand the impact of each of these categories and their various combinations. Then, the impact of different parts of the CovidDeep training process, pre-training with synthetic data, and grow-and-prune synthesis are analyzed.

Since there are six data categories from which the corresponding features are obtained, there are 64 subsets. However, one of these subsets is the null subset. Thus, the remaining 63 subsets are evaluated. For these evaluations, the first two types of DNN models are considered only, referred to as DNN Models 1 and 2. Grow-and-prune synthesis-based models are considered later. The results shown in the table in FIG. 11 correspond to the case when features from only one, two or three data categories are chosen, and in the table in FIG. 12 when features from four, five or six data categories are chosen.

It is first noticed that DNN Model 2 generally performs better than DNN Model 1 across the various performance metrics. This underscores the importance of using synthetic data when the available dataset size is not large. Second, it is observed that since this is a three-way classification, only 33.3% accuracy is possible by randomly predicting one of the three Cohorts. Thus, even single data categories (GSR, Temp, IBI, Ox, BP, Q) enable much better prediction than by chance. These single data categories are still only weak learners of the correct label, when used in isolation. Third, DNN models, in general, tend to perform better on the various performance metrics when more data categories are used. However, this is not always true. For example, the highest accuracy of 93.6% was obtained with DNN Model 2 when only features from four (GSR, Temp, Ox, BP) of the six categories are used. Adding features based on IBI or Q or both to these four categories actually reduces the test accuracy. This may be due to the curse of dimensionality. When the number of features increases, in general, the dataset size needs to be increased to obtain a good accuracy. For a fixed dataset size, this curse indicates that the number of features should be reduced. However, throwing out informative features would also reduce accuracy. In addition, some features are interactive, i.e., work synergistically to increase accuracy. Hence, a balance has to be found between accuracy and the number of features. Finally, when not all sensors are available (perhaps due to cost reasons), a suitable set that still provides reasonable accuracy can be chosen based on the given cost budget. This may help a broader cross-section of the population access the technology.

To illustrate the effect of the different parts of the CovidDeep training process, 11 CovidDeep DNN models are compared, trained based on the different DNN synthesis and training steps. The models were chosen from different accuracy ranges. The table in FIG. 13 shows comparison results for the three-way classification task. Various performance metrics were already compared for DNN Models 1 and 2 earlier. Hence, here, their accuracy, FLOPs, and number of model parameters (#Param) are reported. The best DNN Model 3 was obtained with the help of the validation dataset. This enabled finding the best #Param. value. Only this model was tested on the test dataset. Acc.(1)

and Acc.(2), respectively, refer to the accuracy of DNN Models 1 and 2. The FLOPs and #Param. for these two models are identical. All the performance metrics for DNN Model 3 that is generated by grow-and-prune synthesis using both real and synthetic data are reported. Thus, the starting point for DNN Model 3 synthesis is DNN Model 2. Next, DNN Model 3 is compared with the other two models based on various measures and is shown why it is suitable for deployment on the edge devices.

Smaller model size: It contains 3.4× fewer parameters on an average (geometric mean) than DNN Models 1 and 2, thus significantly reducing the memory requirements.

Less computation: It reduces FLOPs per inference by 3.5× on an average (geometric mean) relative to DNN Models 1 and 2, thus facilitating more efficient inference on the edge devices.

Better performance: It improves accuracy on an average by 7.8% (1.9%) relative to DNN Model 1 (2), while also lowering FPR and FNRs, in general.

CONCLUSION

An interesting ability of the human brain is to efficiently solve novel problems in a new domain despite limited prior experience. Inspired by this human capability, CovidDeep uses the TUTOR approach for synthetic data generation and labeling to help the neural network start from a better initialization point. Use of gradient descent from a learned initialization point provides the DNN with an appropriate inductive bias. Hence, it reduces the need for large datasets that are not readily available for SARS-CoV-2/COVID-19 AI research.

The CovidDeep DNN training process takes another inspiration from the human brain development process in the grow-and-prune synthesis step. The human brain undergoes dynamic changes in its synaptic connections every second of its lifetime. Acquisition of knowledge depends on these synaptic rewirings. Inspired by this phenomenon, CovidDeep utilizes the grow-and-prune synthesis paradigm to enable DNN architecture adaptation throughout training. CovidDeep DNNs synthesized with grow-and-prune synthesis do not suffer from the situation faced by most current DNNs: fixed connections during training. This enables CovidDeep to generate very compact, yet accurate, models for SARS-CoV-2/COVID-19 detection.

CovidDeep uses physiological signals extracted using commercially available devices and achieves high test accuracy. As a result, it provides a testing mechanism that is accurate, easily accessible to the general public, and easy for individuals to use. Furthermore, this mechanism only requires a few minutes of data collection from an individual to perform an inference. Note that at most one hour of data collection from each individual was only required for training of the DNN models. It does not require the presence of a nurse or physician during testing. In fact, besides the data collected by the smartwatch and discrete sensors (for obtaining blood oxygen and blood pressure), the additional information required by the electronic questionnaire is small, related to the general health of the subject, and can be easily filled out with a yes/no answer. Thus, CovidDeep has the potential to significantly decrease the spread of SARS-CoV-2, save hundreds of thousands of lives, and drastically reduce the need for hospitalization, while also helping the world economy recover.

As such, generally disclosed herein are embodiment for a framework called CovidDeep to facilitate daily and pervasive detection of SARS-CoV-2/COVID-19. The framework combines off-the-shelf WMSs with efficient DNNs to achieve this goal. CovidDeep DNNs can be easily deployed on edge devices (e.g., smartphones and smartwatches) as well as servers. CovidDeep uses synthetic data generation to alleviate the need for large datasets. In addition, training of CovidDeep DNNs based on the grow-and-prune synthesis paradigm enables them to learn both the weights and the architecture during training. CovidDeep was evaluated based on data collected from 87 individuals. The highest accuracy it achieves is 98.1%. However, several subsets of features that correspond to easily accessible sensors in the market also achieve high enough accuracy to be practically useful.

It is understood that the above-described embodiments are only illustrative of the application of the principles of the present invention. The present invention may be embodied in other specific forms without departing from its spirit or essential characteristics. All changes that come within the meaning and range of equivalency of the claims are to be embraced within their scope. Thus, while the present invention has been fully described above with particularity and detail in connection with what is presently deemed to be the most practical and preferred embodiment of the invention, it will be apparent to those of ordinary skill in the art that numerous modifications may be made without departing from the principles and concepts of the invention as set forth in the claims.

What is claimed is:

1. A machine-learning based system for coronavirus detection, comprising one or more processors configured to interact with a plurality of wearable medical sensors (WMSs), the processors configured to:
   receive physiological data from the WMSs and questionnaire data from a user interface;
   train at least one neural network based on raw physiological data and questionnaire data augmented with synthetic data and subjected to a grow-and-prune paradigm to generate at least one coronavirus inference model; and
   output a coronavirus-based decision by inputting the received physiological data and questionnaire data into the generated coronavirus inference model,
   wherein the grow-and-prune paradigm comprises the neural network growing at least one of connections and neurons based on gradient information and pruning away at least one of connections and neurons based on magnitude information, and
   wherein the growing at least one of connections and neurons based on gradient information comprises adding connection or neuron when its gradient magnitude is greater than a predefined percentile of gradient magnitudes based on a growth ratio.

2. The system of claim 1, wherein the physiological data comprises at least one of Galvanic skin response and inter-beat interval.

3. The system of claim 2, wherein inter-beat interval indicates at least one of heart rate, skin temperature, oxygen saturation, and blood pressure.

4. The system of claim 1, wherein questionnaire data comprises yes/no answers for at least one of immunocompromised, chronic lung disease, cough, shortness of breath, chills, fever, muscle pain, headache, sore throat, smell-taste loss, and diarrhea.

5. The system of claim 1, wherein the pruning away at least one of connections and neurons based on magnitude information comprises removing a connection or neuron when its magnitude is less than a predefined percentile of magnitudes based on a pruning ratio.

6. The system of claim 1, wherein the grow-and-prune paradigm is iterative.

7. The system of claim 1, wherein outputting a coronavirus-based decision comprises data preprocessing, synthetic data generation and neural network pre-training, grow-and-prune synthesis, and output generation.

8. The system of claim 7, wherein data preprocessing comprises data normalization and data alignment.

9. The system of claim 7, wherein synthetic data generation comprises using at least one of multi-variate normal distribution, Gaussian mixture model, and kernel density estimation.

10. The system of claim 7, wherein synthetic data generation comprises building a knowledge base based on the raw physiological data and questionnaire data.

11. A machine-learning based method for coronavirus detection, based on one or more processors configured to interact with a plurality of wearable medical sensors (WMSs), the method comprising:
    receiving physiological data from the WMSs and questionnaire data from a user interface;
    training at least one neural network based on raw physiological data and questionnaire data augmented with synthetic data and subjected to a grow-and-prune paradigm to generate at least one coronavirus inference model; and
    outputting a coronavirus-based decision by inputting the received physiological data and questionnaire data into the generated coronavirus inference model,
    wherein the grow-and-prune paradigm comprises the neural network growing at least one of connections and neurons based on gradient information and pruning away at least one of connections and neurons based on magnitude information, and
    wherein the growing at least one of connections and neurons based on gradient information comprises adding connection or neuron when its gradient magnitude is greater than a predefined percentile of gradient magnitudes based on a growth ratio.

12. The method of claim 11, wherein the physiological data comprises at least one of Galvanic skin response and inter-beat interval.

13. The method of claim 12, wherein inter-beat interval indicates at least one of heart rate, skin temperature, oxygen saturation, and blood pressure.

14. The method of claim 11, wherein questionnaire data comprises yes/no answers for at least one of immunocompromised, chronic lung disease, cough, shortness of breath, chills, fever, muscle pain, headache, sore throat, smell-taste loss, and diarrhea.

15. The method of claim 11, wherein the pruning away at least one of connections and neurons based on magnitude information comprises removing a connection or neuron when its magnitude is less than a predefined percentile of magnitudes based on a pruning ratio.

16. The method of claim 11, wherein the grow-and-prune paradigm is iterative.

17. The method of claim 11, wherein outputting a coronavirus-based decision comprises data preprocessing, synthetic data generation and neural network pre-training, grow-and-prune synthesis, and output generation.

18. The method of claim 17, wherein data preprocessing comprises data normalization and data alignment.

19. The method of claim 17, wherein synthetic data generation comprises using at least one of multi-variate normal distribution, Gaussian mixture model, and kernel density estimation.

20. The method of claim 17, wherein synthetic data generation comprises building a knowledge base based on the raw physiological data and questionnaire data.

21. A non-transitory computer-readable medium having stored thereon a computer program for execution by a processor configured to perform a machine-learning based method for coronavirus detection, the method comprising:
    receiving physiological data from the WMSs and questionnaire data from a user interface;
    training at least one neural network based on raw physiological data and questionnaire data augmented with synthetic data and subjected to a grow-and-prune paradigm to generate at least one coronavirus inference model; and
    outputting a coronavirus-based decision by inputting the received physiological data and questionnaire data into the generated coronavirus inference model,
    wherein the grow-and-prune paradigm comprises the neural network growing at least one of connections and neurons based on gradient information and pruning away at least one of connections and neurons based on magnitude information, and
    wherein the growing at least one of connections and neurons based on gradient information comprises adding connection or neuron when its gradient magnitude is greater than a predefined percentile of gradient magnitudes based on a growth ratio.

22. The non-transitory computer-readable medium of claim 21, wherein the physiological data comprises at least one of Galvanic skin response and inter-beat interval.

23. The non-transitory computer-readable medium of claim 22, wherein inter-beat interval indicates at least one of heart rate, skin temperature, oxygen saturation, and blood pressure.

24. The non-transitory computer-readable medium of claim 21, wherein questionnaire data comprises yes/no answers for at least one of immunocompromised, chronic lung disease, cough, shortness of breath, chills, fever, muscle pain, headache, sore throat, smell-taste loss, and diarrhea.

25. The non-transitory computer-readable medium of claim 21, wherein the pruning away at least one of connections and neurons based on magnitude information comprises removing a connection or neuron when its magnitude is less than a predefined percentile of magnitudes based on a pruning ratio.

26. The non-transitory computer-readable medium of claim 21, wherein the grow-and-prune paradigm is iterative.

27. The non-transitory computer-readable medium of claim 21, wherein outputting a coronavirus-based decision comprises data preprocessing, synthetic data generation and neural network pre-training, grow-and-prune synthesis, and output generation.

28. The non-transitory computer-readable medium of claim 27, wherein data preprocessing comprises data normalization and data alignment.

29. The non-transitory computer-readable medium of claim 27, wherein synthetic data generation comprises using at least one of multi-variate normal distribution, Gaussian mixture model, and kernel density estimation.

30. The non-transitory computer-readable medium of claim 27, wherein synthetic data generation comprises building a knowledge base based on the raw physiological data and questionnaire data.

31. A machine-learning based system for coronavirus detection, comprising one or more processors configured to interact with a plurality of wearable medical sensors (WMSs), the processors configured to:
receive physiological data from the WMSs and questionnaire data from a user interface;
train at least one neural network based on raw physiological data and questionnaire data augmented with synthetic data to generate at least one coronavirus inference model; and
output a coronavirus-based decision by inputting the received physiological data and questionnaire data into the generated coronavirus inference model,
wherein the grow-and-prune paradigm comprises the neural network growing at least one of connections and neurons based on gradient information and pruning away at least one of connections and neurons based on magnitude information, and
wherein the growing at least one of connections and neurons based on gradient information comprises adding connection or neuron when its gradient magnitude is greater than a predefined percentile of gradient magnitudes based on a growth ratio.

32. The system of claim 31, wherein the physiological data comprises at least one of Galvanic skin response and inter-beat interval.

33. The system of claim 32, wherein inter-beat interval indicates at least one of heart rate, skin temperature, oxygen saturation, and blood pressure.

34. The system of claim 31, wherein questionnaire data comprises yes/no answers for at least one of immunocompromised, chronic lung disease, cough, shortness of breath, chills, fever, muscle pain, headache, sore throat, smell-taste loss, and diarrhea.

35. The system of claim 31, wherein outputting a coronavirus-based decision comprises data preprocessing, synthetic data generation and neural network pre-training, and output generation.

36. The system of claim 35, wherein data preprocessing comprises data normalization and data alignment.

37. The system of claim 35, wherein synthetic data generation comprises using at least one of multi-variate normal distribution, Gaussian mixture model, and kernel density estimation.

38. The system of claim 35, wherein synthetic data generation comprises building a knowledge base based on the raw physiological data and questionnaire data.

* * * * *